(12) United States Patent
Kohayakawa (10) Patent No.: US 6,304,723 B1
(45) Date of Patent: *Oct. 16, 2001

(54) RETINAL CAMERA

(76) Inventor: Yoshimi Kohayakawa, c/o Canon Kabushiki Kaisha 30-2, 3-chome, Shimomaruko, Ohta-ku, Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 3 days.

(21) Appl. No.: 08/899,391

(22) Filed: Jul. 23, 1997

Related U.S. Application Data (63) Continuation of application No. 08/541,626, filed on Oct. 10, 1995, now abandoned.

(30) Foreign Application Priority Data

Oct. 11, 1994 (JP) .................................................... 6-272960
Feb. 1, 1995 (JP) .................................................... 7-037550

(51) Int. Cl.[7] ................................ G03B 29/00; A61B 3/14
(52) U.S. Cl. .............................................................. 396/18
(58) Field of Search ........................ 396/14, 18; 351/206, 351/210, 211, 221; 348/77, 78

(56) References Cited

U.S. PATENT DOCUMENTS

| | | |
|---|---|---|
| 4,452,517 * | 6/1984 | Kohayakawa ........................ 354/62 |
| 4,697,895 | 10/1987 | Sekiguchi et al. . |
| 4,704,012 | 11/1987 | Kohayakawa et al. . |
| 4,820,037 | 4/1989 | Kohayakawa et al. . |
| 5,037,194 | 8/1991 | Kohayakawa et al. . |
| 5,144,346 | 9/1992 | Nakamura et al. . |
| 5,231,430 | 7/1993 | Kohayakawa . |
| 5,237,351 | 8/1993 | Kohayakawa et al. . |
| 5,249,003 | 9/1993 | Kohayakawa . |
| 5,255,026 * | 10/1993 | Arai et al. ............................ 351/206 |
| 5,280,313 | 1/1994 | Kohayakawa . |
| 5,325,134 | 6/1994 | Kohayakawa . |
| 5,371,557 * | 12/1994 | Nanjho et al. ....................... 351/206 |
| 5,382,988 * | 1/1995 | Nanjo .................................. 351/206 |
| 5,420,650 | 5/1995 | Kohayakawa . |
| 5,504,542 * | 4/1996 | Hino et al. ........................... 351/206 |
| 5,504,543 * | 4/1996 | Ueno .................................... 351/206 |
| 5,572,266 * | 11/1996 | Ohtsuka ................................. 396/18 |

* cited by examiner

Primary Examiner—Christopher E. Mahoney (57) ABSTRACT

A retinal camera has an illuminating system for applying illuminating light to the fundus of an eye to be examined, a photographing system for photographing the fundus of the eye, the photographing system having a focusing lens, a projection system for projecting a focus detecting light beam onto the fundus of the eye by a fixed optical system, and a light position sensor for receiving the reflected light of the focus detecting light beam from the fundus of the eye through the focusing lens, the focus state of the photographing system being detected by the deviation of the light beam received by the light position sensor from a predetermined position.

7 Claims, 7 Drawing Sheets

RETINAL CAMERA

This application is a continuation of application Ser. No. 08/541,626 filed Oct. 10, 1995, now abandoned.

BACKGROUND OF THE INVENTION

1. Field of the Invention

This invention relates to a retinal camera for use in ophthalmic hospitals or the like.

2. Related Background Art

A known retinal camera, in which a focusing light beam is not separated in a light-receiving system, has used a focusing light beam projection system having a movable portion and has therefore been complicated in construction.

SUMMARY OF THE INVENTION

This invention has as its object the provision of a retinal camera capable of effecting focus detection by a simple construction.

DESCRIPTION OF THE PREFERRED EMBODIMENTS

The present invention will hereinafter be described in detail with respect to some embodiments thereof shown in the drawings.

Figure 1:
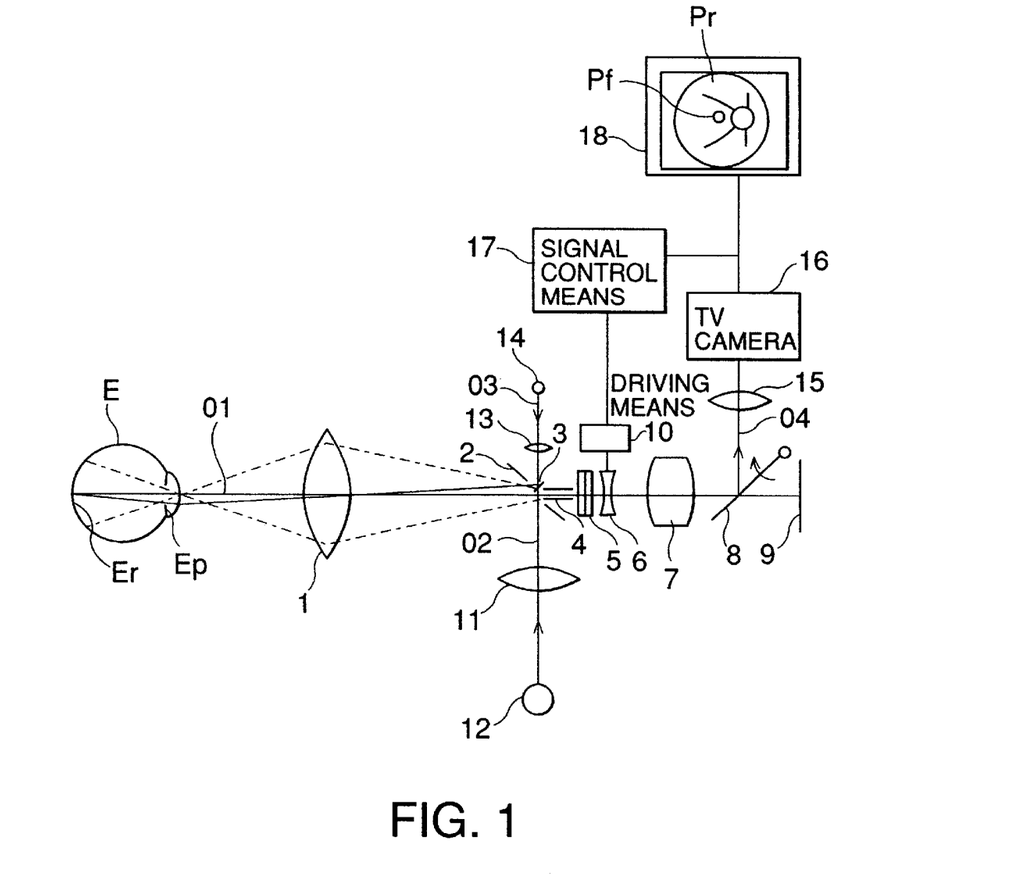
FIG. 1 shows the construction of a first embodiment of the present invention.

Referring to FIG. 1 which shows the construction of a first embodiment, an objective lens 1 is disposed on an optical path 01 in the direction of the visual axis of an eye E to be examined so as to be opposed to the eye E to be examined, and behind the objective lens 1, there are arranged in succession an apertured mirror 2, a small mirror 3 provided in the opening portion of the apertured mirror 2, a photo-taking stop 4 conjugate with the pupil Ep of the eye E to be examined, a cross cylinder lens 5 comprising two cylindrical lenses having the same refractive power, a focusing lens 6, an imaging lens 7, a quick return mirror 8 and film 9. The two cylindrical lenses of the cross cylinder lens 5 may be rotated in opposite directions by driving means 10, and the focusing lens 6 is movable along the optical path 01.

A lens 11 and an eye fundus illuminating light source 12 such as a halogen lamp or a flash tube are arranged on an optical path 02 in the direction of incidence of the apertured mirror 2, and a fixed optical member 13 and a focusing light source 14 are arranged on an optical path 03 in the direction of incidence of the small mirror 3. Further, a lens 15 and a TV camera 16 are arranged on an optical path 04 in the direction of reflection of the quick return mirror 8, and the output of the TV camera 16 is connected to signal control means 17 and a TV monitor 18, and the output of the signal control means 17 is connected to the driving means 10.

When alignment and the observation of the fundus of the eye are performed, the eye fundus illuminating light source 12 and the focusing light source 14 are turned on. A light beam from the eye fundus illuminating light source 12 passes through the lens 11, is reflected by the apertured mirror 2, passes through the objective lens 1 and illuminates the fundus Er or the eye E to be examined. The reflected light beam from the fundus Er of the eye returns along the same optical path, passes through the opening portion of the apertured mirror 2, the photo-taking stop 4, the cross cylinder lens 5, the focusing lens 6 and the imaging lens 7, is reflected by the quick return mirror 8, is picked up as an eye fundus image Pr by the TV camera 16 via the lens 15 and is displayed on the TV monitor 18.

A light beam emitting from the focusing light source 14 passes through the fixed optical member 13, is reflected by the small mirror 3, passes through the objective lens 1 and illuminates the fundus Er of the eye E to be examined as a point. The reflected light beam from the fundus Er of the eye returns along the optical path like the photo-taking light beam from the eye fundus illuminating light source 12, is reflected by the quick return mirror 8, is picked up as a focusing light beam image Pf by the TV camera 16 through the lens 15, and is displayed on the TV monitor 18 with the eye fundus image Pr. The signal control means 17 including a memory and a computer extracts the video signal of the central portion of the image from the TV camera 16, calculates the two-dimensional position of the focusing light beam image Pf, controls the driving means 10 on the basis of the result of this calculation, drives the cross cylinder lens 5 and the focusing lens 6, corrects astigmatism and adjusts the focus.

Figure 2:
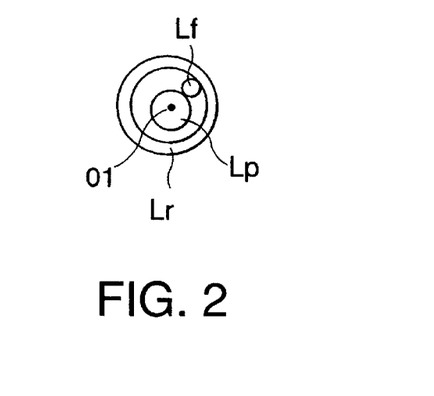
FIG. 2 is an illustration of an eye fundus illuminating light beam, a photographing light beam and a focusing light beam on the pupil of an eye to be examined.

Referring now to FIG. 2 which shows the passage area of the light beam on the surface of the pupil Ep of the eye E to be examined, the eye fundus illuminating light beam Lr by the eye fundus illuminating light source 12 is imaged in the form of a ring on the pupil Ep and is projected onto the fundus Er of the eye, and the reflected light beam from the fundus Er of the eye is taken out as a photo-taking light beam Lp from the inside of the eye fundus illuminating light beam Lr on the pupil Ep by the photo-taking stop 4. Also, the focusing light beam Lf by the focusing light source 14 passes through the area between the eye fundus illuminating light beam Lr and the photo-taking light beam Lp when projected. Then it passes through an area Lp and is received. When the focusing is completed, the focusing light beam image Pf is imaged at a predetermined position on the line of intersection between a plane passing through the optial axis 01 and the center of the focusing light beam Lf and the surface of the fundus Er of the eye. This position differs depending on the refractivity of the eye E. It can be determined from the position of the focusing lens.

Also, in an out-of-focus state, the focusing light beam image Pf deviates from the predetermined position. When the eye E to be examined has astigmatism, the focusing light beam image Pf deviates from the line of intersection. The direction in which it deviates is determined by whether the astigmatism of the eye E to be examined is stronger in vertical refractive power or stronger in horizontal refractive power. Accordingly, the signal control means 17 controls the driving means 10 to thereby rotate the two cylindrical lenses of the cross cylinder lens 5 in opposite directions, and creates astigmatism in a vertical direction or a horizontal direction and corrects the astigmatism of the eye E to be examined so that the focusing light beam image Pf may be positioned on the above-mentioned line of intersection, and further moves the focusing lens 6 along the optical path 01 to thereby form the focusing light beam image Pf at a predetermined position on the line of intersection, thus focusing the eye fundus image Pr. When the eye fundus image Pr is focused, the quick return mirror 8 is jumped up and at the same time, the photo-taking light source of the eye fundus illuminating light source 12 is made to emit light, whereby the eye fundus image Pr is recorded on the film 9.

The cross cylinder lens 5 can be eliminated to simplify the construction. In such case, the astigmatism of the eye E to be examined cannot be completely corrected, but yet the focusing lens 6 can be moved along the optical path 01 so that the focusing light beam image Pf may be formed at the position of a minimum blur circle on the fundus Er of the eye in order to bring the received position of the focusing light beam image Pf closest to a predetermined position.

Also, not an automatic focusing operation but a manual focusing operation by visual confirmation is possible. In such case, a focusing mark indicative of the position of the focusing light beam image Pf calculated from the position of the focusing lens 6 is displayed on the TV monitor 18 and an examiner adjusts the cross cylinder lens 5 and the focusing lens 6 so that this focusing mark and the focusing light beam image Pf may coincide with each other.

Figure 3:
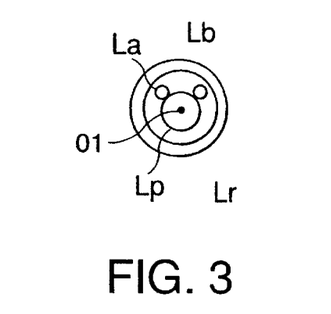
FIG. 3 is an illustration of the eye fundus illuminating light beam, the photographing light beam and the focusing light beam on the pupil of the eye to be examined.
Figure 4:
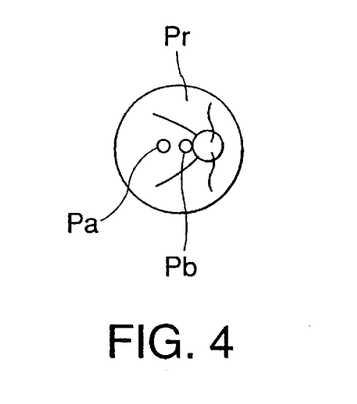
FIG. 4 is an illustration of the image of the fundus of the eye and two focusing light beam images.

The above mentioned embodiment, however, cannot detect the astigmatism in a meridional direction perpendicular to a line passing through the center of the photo-taking light beam Lp and the center of the focusing light beam Lf. Detecting the astigmatism in this meridional direction becomes possible by making two focusing light beams La and Lb enter the pupil Ep of the eye E to be examined and projecting it onto the fundus Er of the eye, as shown in FIG. 3, and receiving two focusing light beam images Pa and Pb as shown in FIG. 4. It is to be understood here that the line passing through the center of the photo-taking light beam Lp and the center of the focusing light beam La is perpendicular to a line linking the focusing light beams Lp and Lb together. In this case, two focusing light sources can be used or a light beam from a focusing light source can be divided into two beams by a stop having two openings.

As the two-dimensional positions of the focusing light beam images Pa and Pb are calculated by the signal control means 17, the degree and the angle of astigmatism of the eye E to be examined can be completely found from this positional information. That is, the refractive values in three meridional directions can be known from the spacings between the light beams Pa and Pb in the directions of the light beams La and Lb, the positions of the light beam Pa in the directions of the light beams La and Lp, and the positions of the light beam Pb in the directions of the light beams Lb and Lp. The signal control means 17 controls the driving means 10 on the basis of this astigmatism information to thereby rotate the two cylindrical lenses of the cross cylinder lens 5 in opposite directions and completely correct the astigmatism of the eye E to be examined.

Figure 5:
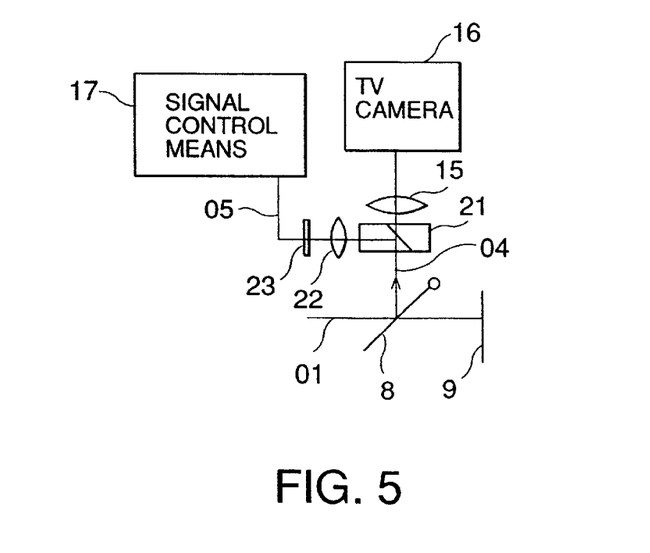
FIG. 5 shows the construction of only the essential portions of a second embodiment of the present invention.

FIG. 5 shows the construction of only the essential portions of a second embodiment of the present invention, and the other portions of this embodiment are the same as those of the first embodiment. On an optical path 04, a dichroic prism 21 is disposed between the quick, return mirror 8 and the lens 15, and a lens 22 and a two-dimensional CCD 23 are arranged on an optical path 05 in the direction of reflection of the dichroic prism 21, the output of the two-dimensional CCD 23 being connected to signal control means 17. The eye fundus illuminating light source 12 and the focusing light source 14 emit light beams of different wavelengths, and the dichroic prism 21 has the wavelength selecting characteristic of transmitting the light beam of the eye fundus illuminating light source 12 therethrough and reflecting the light beam of the focusing light source 14.

Figure 6:
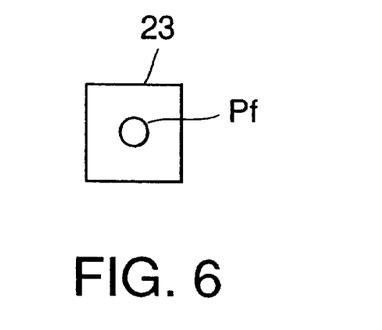
FIG. 6 is a front view of a two-dimensional CCD receiving a focusing light beam image.

Accordingly, only the eye fundus image Pr is picked up by the TV camera 16, and the focusing light beam Lf emitted from the focusing light source 14 is reflected by the dichroic prism 21, passes through the lens 22 and is received as a focusing light beam image Pf by the two-dimensional CCD 23 as shown in FIG. 6. The signal control means 17 introduces this light reception signal thereinto, calculates the two-dimensional position of the focusing light beam image Pf, and drives the cross cylinder lens 5 and the focusing lens 6 so that the focusing light beam image Pf may be received at a predetermined position, thereby focusing the eye fundus image Pr.

Figure 7:
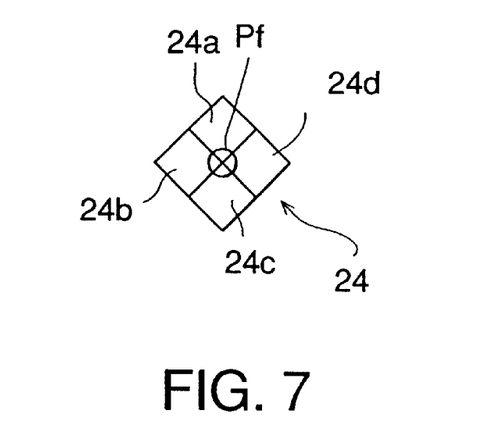
FIG. 7 is a front view of a photosensor receiving the focusing light beam image.

A photosensor 24 comprising four light receiving elements 24a, 24b, 24c and 24d as shown in FIG. 7 can also be used instead of the two-dimensional CCD 23. It is to be understood that the dividing lines between the light receiving elements 24a and 24b and between the light receiving elements 24d and 24c are perpendicular to the center line of the focusing light beams Lf and Lp. In this case, the focusing lens 6 is driven so that the sum of the light reception signals of the pair of light receiving elements 24a and 24d of the photosensor 24 and the sum b of the light reception signals of the light receiving elements 24b and 24c may become equal to each other. Also, the cross cylinder lens 5 is driven so that the sum of the light reception signals of the other pair of light receiving elements 24a and 24b and the sum b of the light reception signals of the light receiving elements 24d and 24c may become equal to each other. When focused, the focusing light beam image Pf is bisected by the border line of the light receiving elements 24a, 24b, 24c and 24d of the photosensor 24 as shown in FIG. 7.

Figure 8:
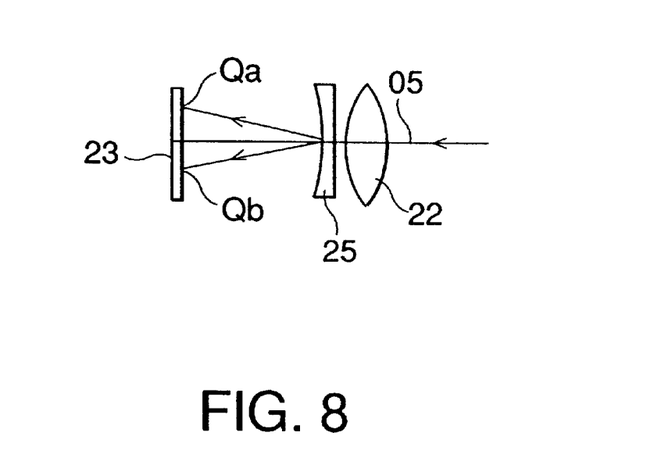
FIG. 8 shows the construction of only the essential portions of a third embodiment of the present invention.

FIG. 8 shows the construction of only the essential portions of a third embodiment of the present invention. In this embodiment which is a modification of the second embodiment shown in FIG. 5, a wedge prism 25 comprising two wedge prisms disposed in opposite directions on a plane conjugate with the pupil Ep of the eye E to be examined behind the lens 22 is inserted in an optical path 05 in the direction of reflection of the dichroic prism 21. In this case, focusing becomes possible by only the light beam passing through the photo-taking stop 4.

Figure 9:
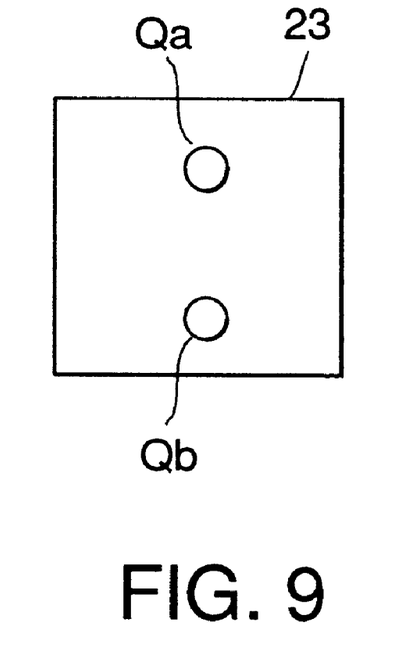
FIG. 9 is a front view of the two-dimensional CCD receiving two focusing light beam images when the eye to be examined has no astigmatism.

The focusing light beam Lf reflected by the dichroic prism 21 passes through the lens 22 and is divided into two light beams by the wedge prism 25, and the two light beams are received as focusing light beam images Qa and Qb by the two-dimensional CCD 23. In a state in which the eye fundus image Pr is out of focus when the eye E to be examined is free of astigmatism, the focusing light beam images Qa and Qb deviate from each other in a vertical direction in which the pupil is divided from a predetermined distance determined by the wedge angle, as shown in FIG. 9.

Figure 10:
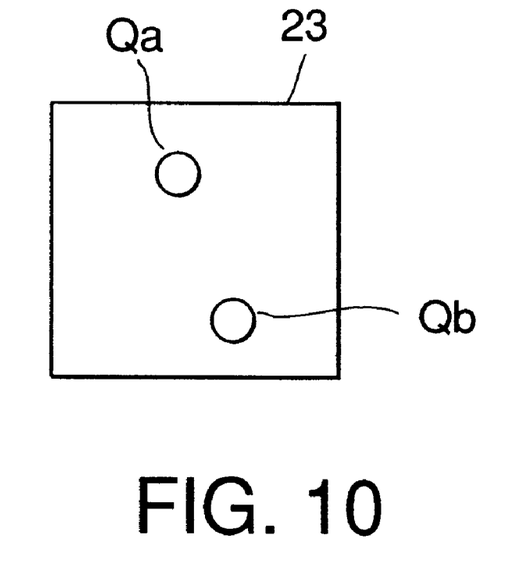
FIG. 10 is a front view of the two-dimensional CCD receiving two focusing light beam images when the eye to be examined has astigmatism.

On the other hand, when the eye E to be examined has astigmatism, the focusing light beam images Qa and Qb deviate from each other also in a horizontal direction, as shown in FIG. 10. The signal control means 17 finds the two-dimensional received positions of the focusing light beam images Qa and Qb, adjusts the cross cylinder lens 5 and corrects the horizontal deviation between the focusing light beam images Qa and Qb, whereafter it adjusts the focusing lens 6 and corrects the vertical deviation between the focusing light beam images Qa and Qb, thereby focusing the eye fundus image Pr.

While in the foregoing description, the focusing light beam Lf is reflected by the small mirror 3 and is projected onto the fundus Er of the eye E to be examined, the design of the may also be made such that the focusing light beam beam Lf is reflected by the apertured mirror 2 through a portion of the illuminating optical path 02 and is projected onto the fundus Er of the eye E to be examined. Particularly, in the third embodiment of FIG. 8, the focusing light beam Lf can also be projected while being superposed on the ring-shaped eye fundus illuminating light beam Lr as shown in FIG. 2. The focusing light beam Lf is projected so as to pass through the inside of the eye fundus illuminating light beam Lr, whereby the focusing light beam Lf comes closer to the photo-taking light beam Lp than the eye fundus illuminating light beam Lr, and this leads to the advantage that it is difficult for the focusing light beam Lf to be affected by the aberration of the eyeball of the eye E to be examined.

Figure 11:
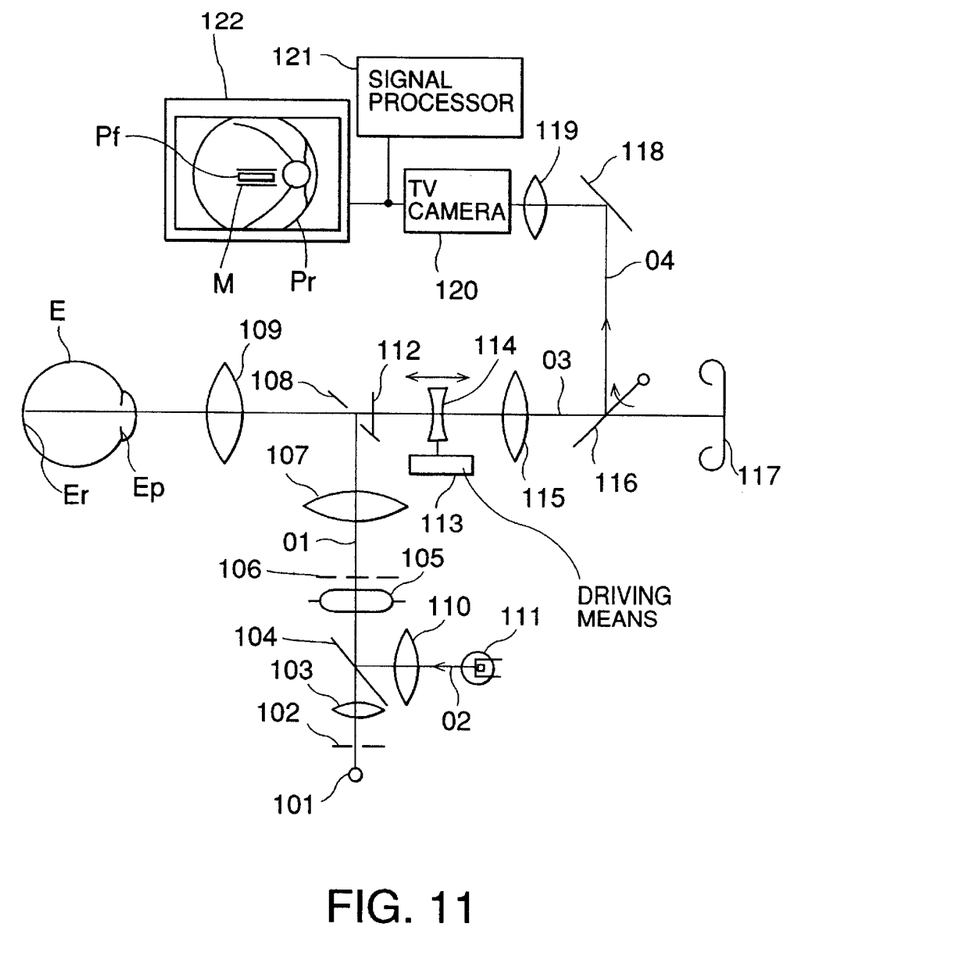
FIG. 11 shows the construction of a fourth embodiment of the present invention.

FIG. 11 shows the construction of a fourth embodiment of the present invention. This embodiment is an example of a non-mydriatic type retinal camera. On an optical path 01 leading from a focusing light source 101 to the eye E to be examined, there are arranged in succession a stop 102 conjugate with the fundus Er of the emmetropia eye E to be examined, a lens 103, a dichroic mirror 104 reflecting a light beam of a wavelength of the order of 800 nm or greater, a photo-taking light source 105 such as a flash light source, a ring stop 106 conjugate with the pupil Ep, a lens 107, an apertured mirror 108 and an objective lens 109. Also, on an optical path 02 in the direction of reflection of the dichroic mirror 104, there are arranged a lens 110 and an observation light source 111 emitting an infrared light beam.

Figure 12:
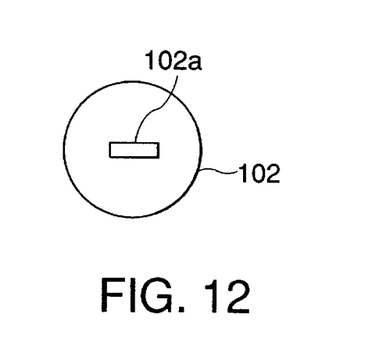
FIG. 12 is a front view of a stop.

Referring to FIG. 12 which is a front view of the stop 102, there is provided a rectangular or slit-like opening 102a near the center of the stop 102. Although this stop 102 is not always necessary, it is preferable that the stop 102 be arranged when focusing is effected by visually looking at the image on the TV monitor. Also, the focusing light source 101 is conjugate with the pupil Ep of the eye E to be examined, and comprises a near infrared LED or the like emitting a light beam having a peak in a near infrared light beam of a wavelength of 800 nm or less, and is disposed at a location somewhat deviating from the optical path 01.

Also, on an optical path 03 behind the apertured mirror 108, there are arranged in succession a photo-taking stop 112, a focusing lens 114 movable along the optical path 03 by driving means 113, an imaging lens 115, a quick return mirror 116 and film 117.

Further, on an optical path 04 in the direction of reflection of the quick return mirror 116, there are arranged in succession a mirror 118, a lens 119 and a TV camera 120 such as a CCD camera, and this TV camera 120 has connected thereto a signal processor 121 provided with a character generator and a computer for calculating a video signal and focusing it, and a TV monitor 122.

A light beam from the observation light source 111 passes through the lens 110, is reflected by the dichroic mirror 104, passes through the photo-taking light source 105, the ring stop 106 and the lens 107, is reflected by the apertured mirror 108, enters the pupil Ep via the objective lens 109 and illuminates the fundus Er of the eye. Also, a light beam from the focusing light source 101 passes through the stop 102, the lens 103 and the dichroic mirror 104, passes along the same optical path as the light beam from the observation light source 111 and is projected from a part of the pupil onto the fundus Er of the eye.

Figure 13:
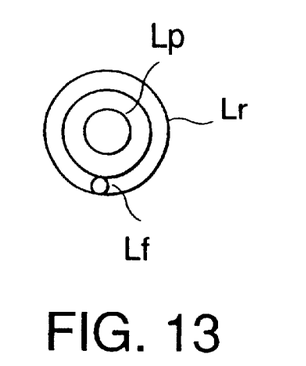
FIG. 13 illustrates the positional relation between light beams on the surface of the pupil.

FIG. 13 is an illustration of the positional relation between light beam on the surface of the pupil Ep. A ring light beam Lr by the ring stop 106 is projected around the central photo-taking light beam Lp by the photo-taking stop 112. Since the focusing light source 101 deviates a little from the optical axis of the optical path 01, a focusing light beam Lf by the focusing light source 101 is projected from below the photo-taking light beam Lp.

The reflected light beam from the fundus Er of the eye returns along the same optical path, passes through the apertured mirror 108, the photo-taking stop 112, the focusing lens 114 and the imaging lens 115, is the focusing lens 114 and the imaging lens 115, is reflected by the quick return mirror 116 and the mirror 118, passes through the lens 119 and is received by the TV camera 120. Two line focusing mark M created in the character generator in the signal processor 121 and the focusing light beam image Pf by the focusing light beam Lf are displayed on the TV monitor 122 with the eye fundus image Pr.

During the focusing operation, the driving means 113 is driven so that the focusing light beam image Pf may be intermediate between the two lines of the focusing mark M, thereby moving the focusing lens 114 to effect focusing. The displayed position of the focusing mark M is calculated by the computer in the signal processor 121 from the position of the focusing lens 114. The position of the focusing mark M moves up and down with the movement of the focusing lens 114.

When the examiner is to effect focusing by visual confirmation, he manually moves the focusing lens 114 to thereby effect focusing while observing the focusing light beam image Pf and the focusing mark M on the TV monitor 122. When in focus, the focusing light beam image Pf is at the intermediate position between the lines of focusing mark M also on the TV monitor 122, but when not in focus, the focusing mark M deviates vertically from the intermediate position of the focusing light beam image Pf. Also, if the focusing light beam Lf enters the pupil Ep from the lateral direction of the photo-taking light beam Lp, the focusing light beam image Pf will be laterally moved by defocus. In this manner, the focusing light beam image Pf moves by defocusing in the meridional direction passing through the center of the photo-taking light beam Lp and the center of the focusing light beam Lf. Therefore, the examiner judges the position in that direction and effects focusing.

On the other hand, when focusing is to be effected by auto-focusing, the image is processed by the signal processor 121 by the use of the video signal of the central portion of the image from the TV camera 120 and the vertical position of the focusing light beam image Pf is calculated. From the difference between that position and the position calculated from the position of the focusing lens 114, the signal processor 121 determines the direction and amount of movement of the focusing lens 114, and the focusing lens 114 is moved by the driving means 113 to thereby effect focusing.

The focusing operation is performed in this manner, and after focusing, the examiner pushes a photographing button, and in synchronism with the jumping up of the quick return mirror 116, the photo-taking light source 105 emits light and the eye fundus image Pr is recorded on the film 117.

Figure 14:
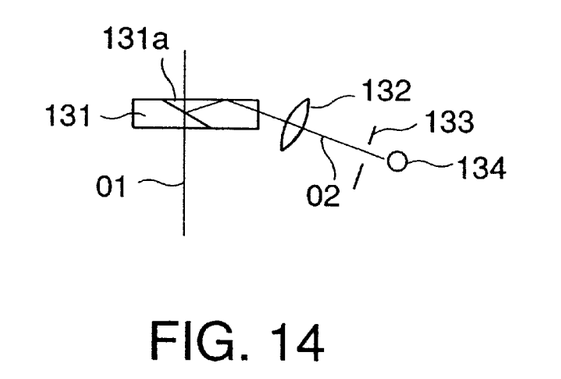
FIG. 14 shows the construction of a focusing light beam projection system in a fifth embodiment of the present invention.

Referring to FIG. 14 which shows the construction of a focusing light beam projection system in a fifth embodiment which is a modification of the fourth embodiment, a flat prism 131 provided with a reflecting surface 131a is disposed on the optical path 01 of the fourth embodiment, and a lens 132, a stop 133 conjugate with the fundus Er of the eye and a focusing light source 134 are arranged in succession in the direction of incidence of the flat prism 131.

A light beam from the focusing light source 134 passes through the stop 133 and the lens 132, is once totally reflected in the flat prism 131 and is directed to the optical path 01 of FIG. 11. In this case, total reflection is performed in the flat prism 131 and therefore, the angle of incidence onto the reflecting surface 131a becomes small and wavelength division can be effected more efficiently.

Figure 15:
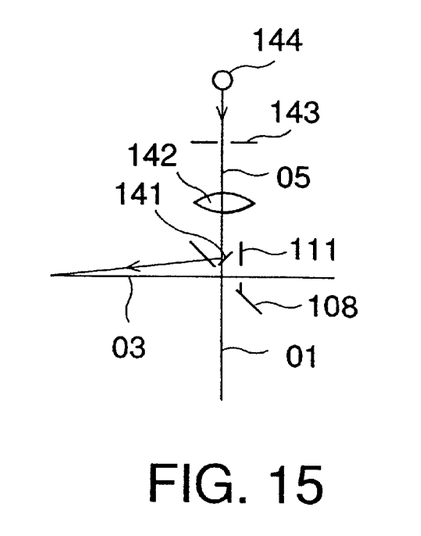
FIG. 15 shows the construction of a focusing light beam projection system in a sixth embodiment of the present invention.

Referring now to FIG. 15 which shows the construction of a focusing light beam projection system in a sixth embodiment which is a modification of the fourth embodiment, a lens 142, a stop 143 conjugate with the fundus Er of the eye, and a focusing light source 144 are arranged on an optical path 05 in the direction of incidence of a small mirror 141 provided near the apertured mirror 108 and photo-taking stop 112 of the fourth embodiment.

A light beam from the focusing light source 144 passes through the stop 143 and the lens 142, is reflected by the small mirror 141 and is directed to an optical path 03. In this case, in FIG. 13, the focusing light beam Lf is projected between the photo-taking light beam Lp and the ring light beam Lr and the focusing light beam Lf becomes near to the photo-taking light beam Lp and therefore, the resolving power becomes poor, but the influence of aberrations in the pupil Ep becomes small.

Figure 16:
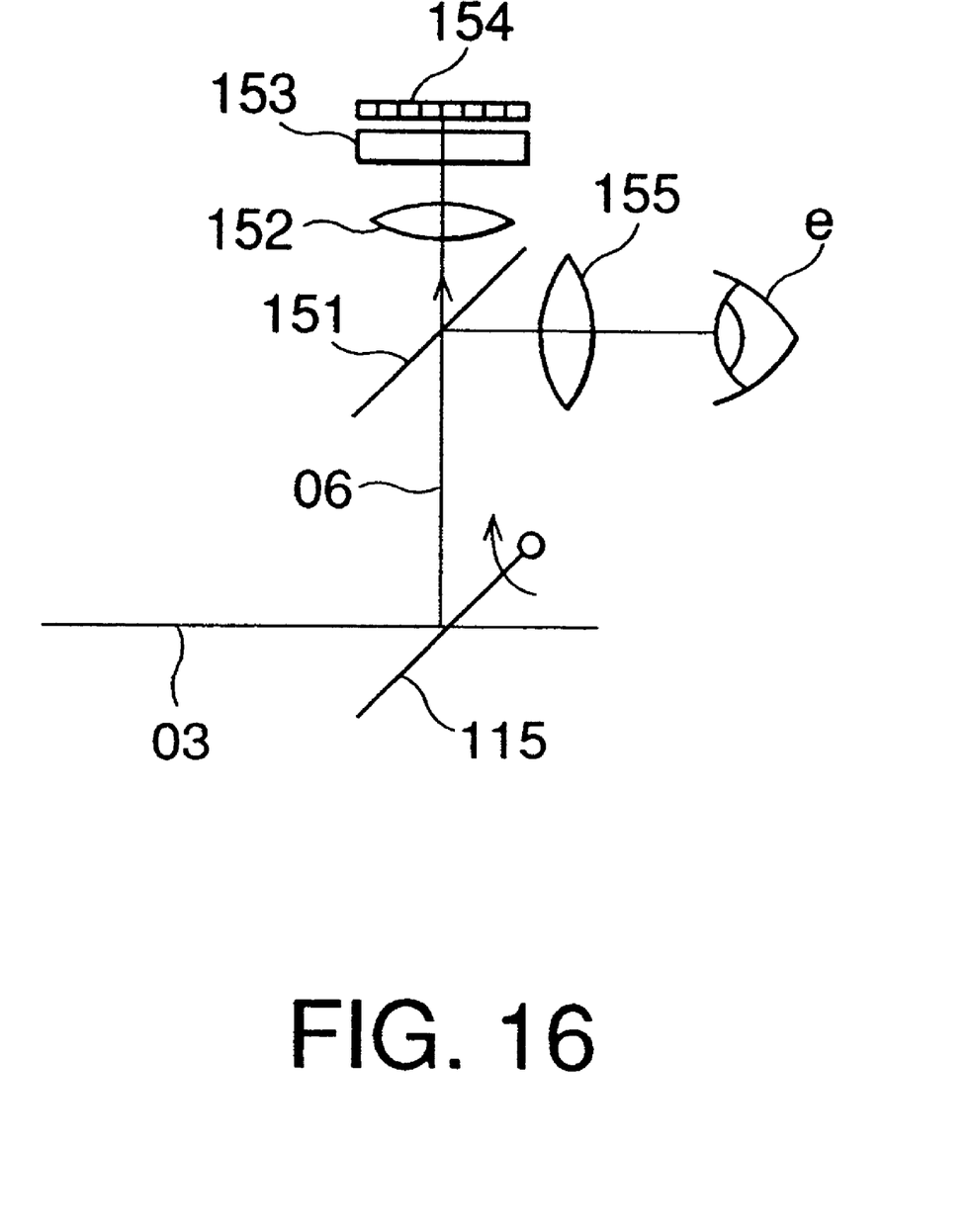
FIG. 16 shows the construction of an observation optical system in a seventh embodiment of the present invention.

FIG. 16 shows the construction of an observation optical system in a seventh embodiment which is a modification of the fourth embodiment. This embodiment is an example of a mydriatic type retinal camera in which the fundus Er of the eye is observed by means of a visible light beam and focusing is effected by a near infrared light beam. Instead of observing by means of the TV monitor 122 of the fourth embodiment, on an optical path 06 in the direction of reflection of the quick return mirror 116 of FIG. 11, there are arranged in succession a dichroic mirror 151 reflecting a visible light beam and transmitting an infrared light beam therethrough, a lens 152, a cylindrical lens 153 having convex power in a direction perpendicular to the plane of the drawing sheet of FIG. 16 and increasing light condensing efficiency, and a one-dimensional CCD 154 disposed parallel to the bus line of the cylindrical lens 153 and conjugate with the surface of the film 117 of FIG. 11. Also, a finder 155 is disposed on an optical path in the direction of reflection of the dichroic mirror 151 so that observation can be done by an examining eye E.

The reflected light beam from the fundus Er of the eye is reflected by the quick return mirror 115, and the focusing light beam from the focusing light source 101 of FIG. 11 passes through the dichroic mirror 151, the lens 152 and the cylindrical lens 153 and is received by the one-dimensional CCD 154. Also, the light beam from the observation light source 111 of FIG. 11 is reflected by the dichroic mirror 151, enters the finder 155, and is observed as the eye fundus image by the examining eye E.

During focusing, a focusing signal which has entered the one-dimensional CCD 154 is calculated by the signal processor 121 and on the basis thereof, the focusing lens 114 is driven by the driving means 113 to thereby effect focusing. Since the position of the focusing light beam which has entered the one-dimensional CCD 154 differs depending on the position of the focusing lens 114, the in-focus position is found in advance and it is displayed by turning on an in-focus display light beam, not shown, in the field of view of the finder 155 that the focusing light beam has been positioned at the in-focus position.

It is also possible to manually drive the focusing lens 114 and display the completion of focusing in the finder 155, instead of effecting auto-focusing.

What is claimed is:

1. A retinal camera comprising:
    an illuminating system which applies illuminating light from an illumination light source to the fundus of an eye to be examined;
    a photographing system which photographs the illuminated fundus of the eye, said photographing system having a stop and a focusing lens;
    a projection system which projects a focus detecting light beam from a light source other than said illumination light source onto the fundus of the eye, without passing through said stop and said focusing lens, by a fixed optical system from a position being eccentric with respect to the optical axis of said photographing system; and
    a light position sensor which receives reflected light of the focus detecting light beam from the fundus of the eye through said stop and said focusing lens, the focus state of said photographing system being detected by the deviation of the light beam received by said light position sensor from a predetermined position.

2. The camera according to claim 1, further comprising a focusing system for effecting the focusing of said photographing system on the basis of the output of said light position sensor.

3. The camera according to claim 1, wherein said light position sensor comprises an image pickup element for picking up the image of the fundus of the eye.

4. The camera according to claim 1, wherein said light position sensor detects the two-dimensional position of the reflected light.

5. The camera according to claim 1, wherein said projection system projects plurality of said focus detecting light beam onto the fundus of the eye.

6. A retinal camera comprising:

an illuminating system which applies illuminating light to the fundus of an eye to be examined;

a photographing system which photographs the fundus of the eye, said photographing system having a stop and a focusing lens;

a projection system which projects a plurality of focus detecting light beams onto plural positions of the fundus of the eye passing through different positions of the pupil of the eye by a fixed optical system; and a light position sensor which receives reflected light of said focus detecting light beams reflected from the fundus of the eye through said stop and said focusing lens, the focus state of said photographing system being detected from the positions of the light beams received by said light position sensor, wherein the plurality of focus detecting light beams and the illuminating light are emitted from different light sources.

7. A retinal camera comprising:

an illuminating system which applies illuminating light to the fundus of an eye to be examined;

a photographing system which photographs the fundus of the eye, said photographing system having a focusing lens;

a projecting system which projects a focus detecting light beam onto the fundus of the eye; and a display for displaying the fundus image of the eye with the projected image of said focus detecting light beam on the eye fundus and a focusing mark electronically generated, wherein the focusing mark is used as a reference mark for adjusting the position of the focus detecting light beam projected on the eye fundus.

* * * * *

UNITED STATES PATENT AND TRADEMARK OFFICE
CERTIFICATE OF CORRECTION

PATENT NO. : 6,304,723 B1
DATED : October 16, 2001
INVENTOR(S) : Yoshimi Kohayakawa It is certified that error appears in the above-identified patent and that said Letters Patent is hereby corrected as shown below:

<u>Title page,</u>
Item [76], "c/o Canon Kabushiki Kaisha 30-2, 3-chome, Shimomaruko, Ohta-ku, Tokyo (JP)" should read -- Yokohama (Japan) --.

Insert: -- [74] *Attorney, Agent, or Firm* — Fitzpatrick, Cella, Harper & Scinto --.

<u>Column 3,</u>
Line 6, "optial" should read -- optical --.

<u>Column 5,</u>
Line 28, "of the" should be deleted.

Signed and Sealed this

Thirteenth Day of May, 2003

JAMES E. ROGAN
*Director of the United States Patent and Trademark Office*

UNITED STATES PATENT AND TRADEMARK OFFICE
CERTIFICATE OF CORRECTION

PATENT NO.    : 6,304,723 B1                                              Page 1 of 1
DATED         : October 16, 2001
INVENTOR(S)   : Yoshimi Kohayakawa It is certified that error appears in the above-identified patent and that said Letters Patent is hereby corrected as shown below:

<u>Title page,</u>
Insert the following:
-- [73] Assignee: Canon Kabushiki Kaisha, Tokyo, (JP) --.

Signed and Sealed this

Twenty-seventh Day of January, 2004

JON W. DUDAS
*Acting Director of the United States Patent and Trademark Office*